(12) United States Patent
Clark et al.

(10) Patent No.: US 7,816,122 B2
(45) Date of Patent: Oct. 19, 2010

(54) LATERAL FLOW DEVICE WITH ONBOARD REAGENTS

(75) Inventors: Scott Marshall Clark, Cape Elizabeth, ME (US); Keith Alan Nassif, Saco, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 89 days.

(21) Appl. No.: 11/253,254

(22) Filed: Oct. 18, 2005

(65) Prior Publication Data

US 2007/0087357 A1   Apr. 19, 2007

(51) Int. Cl.
*C12M 1/348* (2006.01)
(52) U.S. Cl. .................................... 435/287.1
(58) Field of Classification Search ............... 422/55, 422/56, 57, 58, 61, 101; 435/4, 7.1, 287.1, 435/287.2, 287.6, 287.7, 287.9, 970; 436/501, 436/164, 165, 169, 518, 528
See application file for complete search history.

(56) References Cited

U.S. PATENT DOCUMENTS

| | | | | |
|---|---|---|---|---|
| 4,918,025 A * | 4/1990 | Grenner | ...................... | 435/7.94 |
| 4,943,522 A | 7/1990 | Eisinger et al. | | |
| 4,956,302 A | 9/1990 | Gordon et al. | | |
| 4,981,786 A | 1/1991 | Dafforn et al. | | |
| 5,160,701 A * | 11/1992 | Brown et al. | ................... | 422/56 |
| 5,354,692 A | 10/1994 | Yang et al. | | |
| 5,569,608 A | 10/1996 | Sommer | | |
| 5,622,871 A | 4/1997 | May et al. | | |
| 5,726,010 A | 3/1998 | Clark | | |
| 5,726,013 A * | 3/1998 | Clark | ............................ | 435/5 |
| 5,744,096 A * | 4/1998 | Jones et al. | ................... | 422/58 |
| 5,750,333 A * | 5/1998 | Clark | ............................ | 435/5 |
| 5,939,331 A | 8/1999 | Burd et al. | | |
| 5,965,458 A | 10/1999 | Kouvonen et al. | | |
| 6,007,999 A * | 12/1999 | Clark | ......................... | 435/7.1 |
| 6,017,494 A * | 1/2000 | Ashihara et al. | .............. | 422/58 |
| 6,093,546 A * | 7/2000 | Ledden et al. | ................ | 435/7.1 |
| 6,159,747 A * | 12/2000 | Harttig et al. | ............... | 436/518 |
| 6,183,972 B1 | 2/2001 | Kuo et al. | | |
| 6,248,294 B1 * | 6/2001 | Nason | ......................... | 422/58 |
| 6,287,875 B1 | 9/2001 | Geisberg | | |
| 6,365,417 B1 | 4/2002 | Fleming et al. | | |
| 6,436,722 B1 | 8/2002 | Clark et al. | | |
| 6,464,939 B1 | 10/2002 | Bachand et al. | | |
| 6,468,474 B2 | 10/2002 | Bachand et al. | | |
| 6,607,922 B2 | 8/2003 | LaBorde | | |
| 6,617,116 B2 | 9/2003 | Guan et al. | | |
| 6,673,629 B2 | 1/2004 | Yoshimura et al. | | |
| 6,686,208 B2 | 2/2004 | Meusel et al. | | |
| 6,699,722 B2 | 3/2004 | Bauer et al. | | |
| 6,706,539 B2 | 3/2004 | Nelson et al. | | |
| 7,049,150 B2 * | 5/2006 | Bachand | ..................... | 436/518 |
| 7,220,595 B2 * | 5/2007 | Nugent et al. | ............... | 436/514 |
| 7,238,519 B2 * | 7/2007 | Bellet et al. | .............. | 435/287.2 |
| 2002/0173047 A1 * | 11/2002 | Hudak et al. | ................. | 436/178 |
| 2003/0129680 A1 * | 7/2003 | O'Connor, Jr. | ............. | 435/7.32 |
| 2004/0235189 A1 * | 11/2004 | Lu | .............................. | 436/514 |
| 2005/0112023 A1 * | 5/2005 | Liang | .......................... | 422/58 |
| 2005/0164404 A1 * | 7/2005 | Marlborugh et al. | ......... | 436/514 |
| 2005/0227371 A1 * | 10/2005 | Gokhan | ....................... | 436/514 |

\* cited by examiner

*Primary Examiner*—Ann Y Lam
(74) *Attorney, Agent, or Firm*—McDonnell Boehnen Hulbert & Berghoff LLP (57) ABSTRACT

Devices, methods and kits for conducting an assay to determine the presence or amount of an analyte in a fluid sample. The device includes a sample application element and a flow path matrix that facilitates fluidic flow by capillary action. The sample application element includes a non-absorbent or absorbent carrier that has a conjugate reagent that is readily solubilized by the liquid sample. In various aspects of the invention, the sample application element and the matrix are associated with a housing that allows for releasable contact between the element and the matrix. In other aspects, the invention includes methods using the device and kits including the device.

32 Claims, 4 Drawing Sheets

LATERAL FLOW DEVICE WITH ONBOARD REAGENTS

FIELD OF THE INVENTION

The invention relates to lateral flow devices for detecting analytes in fluid samples. More specifically, the invention relates to a lateral flow device having all of the reagents for conducting the detection steps present as part of the device.

BACKGROUND OF THE INVENTION

Lateral-flow type devices for the detection and quantification of an analyte of interest in a fluid sample are well known. Generally, the devices include a solid phase fluid permeable flow paths through which fluid travels by capillary force. The flow paths have immobilized thereon various binding reagents for the analyte (or analog thereof), other binding partners, or conjugates involving binding partners for the analyte and members of signal producing systems (e.g., a label). The various assay formats (e.g. competitive, sandwich, and blocking) used with these devices are well known for the direct or indirect detection of the analyte of interest in the test sample.

In using lateral flow devices to conduct an assay, sample preparation is important to the function of the assay. Importantly, the devices rely on sufficient sample volume so that the matrix can be sufficiently wetted to allow for lateral flow of the sample liquid. Thus, samples often need to be diluted when sample volumes are small. For blood samples, large volumes can be centrifuged to remove red blood cells and other blood components. But for small volumes, such as the volume from a finger prick, centrifuging is not practical. In some cases, the devices include a filter to remove some of the sample's solid or cellular components. In such cases, the filters themselves absorb a significant sample volume.

Sample volume is one way of controlling the sensitivity of the assay, since enough sample is necessary in order to provide a detectable quantity of the analyte. For small volume sample, one way to control sensitivity of the assay is to control how the sample is added to the device. Numerous ways are known for adding sample to solid phase flow paths of lateral flow devices. For instance, sample may be added directly to the flow path or to a sample holder. Such devices are described in U.S. Pat. Nos. 4,943,522; 4,956,302; 5,939,331; 6,468,474; 6,607,922; 6,686,208; and 6,706,539, each of which is incorporated by reference herein in its entirety. In addition to sensitivity, the ease of operator use and the minimization of steps are commercially desirable features. Thus, ways to decrease sample and reagent handling, while maintaining assay sensitivity, are important aspects of developing lateral flow devices.

SUMMARY OF THE INVENTION

The invention is directed to a devices, methods and kits for determining the presence or amount of an analyte in a liquid sample. In one aspect, a device of the invention includes a flow path matrix that provides fluidic movement by capillary force and a sample application element for receiving the sample and transferring the sample to a first region of the matrix. The sample application element has a non-porous carrier for a solubilizable conjugate reagent. The flow path matrix includes an immobilized analyte binding partner in a second region of the matrix that is laterally spaced from the first region. In one aspect, the sample application element and the matrix are associated with a housing that allows for releasable contact between the element and the matrix. The device may also include at least one liquid reagent stored in at least one sealed container, and an absorbent reservoir for absorbing excess liquid from the matrix.

Another aspect of the invention includes a method for determining the presence or amount of an analyte in a biological fluid sample. The method includes providing a device having a flow path matrix that provides fluidic movement by capillary force and a sample application element for receiving the sample and transferring the sample to a first region of the matrix. In the method, the sample application element has a non-porous carrier for a solubilizable conjugate reagent, and the flow path matrix includes an immobilized analyte binding partner in a second region of the matrix that is laterally spaced from the first region. The conjugate reagent is solubilized by adding the sample to the sample application element. The sample and conjugate reagent are allowed to migrate to the second region, and unbound sample and conjugate reagent are washed from the second region. The presence of the conjugate reagent in the second region is detected.

In various aspects of the invention, the sample application element comprises a bead or a disk as a non-porous carrier for the dried conjugate reagent. Also, in an alternate embodiment of the invention, the sample application element can include a porous carrier for the conjugate reagent.

DETAILED DESCRIPTION OF THE INVENTION

The invention provides devices, kits and methods for conducting qualitative or quantitative analysis of selected analytes in samples using the principle of capillary mediated lateral flow through a porous carrier matrix. The invention can be used for a wide variety of assays, both ligand-based and non-ligand-based. Applicable ligand-based methods include, but are not limited to, competitive immunoassays, non-competitive or so-called sandwich technique immunoassays, and blocking assays. The use of the invention is not limited to any particular analyte. The embodiments described herein are solely for illustrative purposes and are not intended to limit the scope of the invention to any particular set of binding partners or assay format.

Before describing the present invention in further detail, a number of terms will be defined. Use of these terms do not limit the scope of the invention but only serve to facilitate the description of the invention. As used herein, the singular forms "a," "an," and "the" include plural referents unless the context clearly dictates otherwise.

By "analyte" is meant a molecule or substance to be detected. For example, an analyte, as used herein, may be a ligand, which is mono- or polyepitopic, antigenic or haptenic; it may be a single compound or plurality of compounds that share at least one common epitopic site; it may also be a receptor or an antibody.

A "sample" refers to an aliquot of any matter containing, or suspected of containing, an analyte of interest. For example, samples include biological samples, such as samples from taken from animals (e.g., saliva, whole blood, serum, and plasma, urine, tears and the like), cell cultures, plants, etc.; environmental samples (e.g., water); and industrial samples. While the device of the invention is appropriate for use with undiluted liquid samples, samples may be prepared prior to use in the methods of the invention. For example, samples may require diluting, filtering, centrifuging or stabilizing prior to use with the invention. For the purposes herein, "sample" refers to the either the raw sample or a sample that has been prepared.

"Binding specificity" or "specific binding" refers to the substantial recognition of a first molecule for a second molecule. Such recognition is displayed, for example, by a polypeptide and a polyclonal or monoclonal antibody, an antibody fragment (e.g. a Fv, single chain Fv, Fab', or F(ab')2 fragment) specific for the polypeptide, enzyme—substrate interactions, and polynucleotide hybridization interactions.

"Non-specific binding" refers to non-covalent binding between molecules that is relatively independent of specific surface structures. Non-specific binding may result from several factors including electrostatic and hydrophobic interactions between molecules.

"Member of a specific binding pair" or "specific binding partner" refers one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, IgG-protein A, polynucleotide pairs such as DNA-DNA, DNA-RNA, and the like are not immunological pairs but are included in the invention and the definition of a specific binding pair member.

"Analyte-specific binding partner" refers to a specific binding partner that is specific for the analyte.

"Substantial binding" or "substantially bind" refer to an amount of specific binding or recognizing between molecules in an assay mixture under particular assay conditions. In its broadest aspect, substantial binding relates to the difference between a first molecule's incapability of binding or recognizing a second molecule, and the first molecule's capability of binding or recognizing a third molecule, such that the difference is sufficient to allow a meaningful assay to be conducted distinguishing specific binding under a particular set of assay conditions, which includes the relative concentrations of the molecules, and the time and temperature of an incubation. In another aspect, one molecule is substantially incapable of binding or recognizing another molecule in a cross-reactivity sense where the first molecule exhibits a reactivity for a second molecule that is less than 25%, preferably less than 10%, more preferably less than 5% of the reactivity exhibited toward a third molecule under a particular set of assay conditions, which includes the relative concentration and incubation of the molecules. Specific binding can be tested using a number of widely known methods, e.g., an immunohistochemical assay, an enzyme-linked immunosorbent assay (ELISA), a radioimmunoassay (RIA), or a western blot assay.

"Ligand" refers any organic compound for which a receptor naturally exists or can be prepared.

"Analyte analog" or "analog of the analyte" refer to a modified form of the analyte which can compete with the analyte for a receptor, the modification providing a way to join the analyte to another molecule. The analyte analog will usually differ from the analyte by more than replacement of a hydrogen with a bond that links the analyte analog to a hub or label, but need not. The analyte analog can bind to the receptor in a manner similar to the analyte.

"Receptor" refers to any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component C1q, penicillin binding protein and the like.

"Antibody" refers to an immunoglobulin that specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab').sub.2, Fab', and the like. In addition, aggregates, polymers, and conjugates of immunoglobulins or their fragments can be used where appropriate so long as binding affinity for a particular molecule is maintained.

"Porous carrier matrix" refers to a solid phase matrix capable of providing capillary mediated lateral flow to a liquid test sample and/or liquid reagents. Generally, the porous carrier matrix can be selected from any available material having appropriate thickness, pore size, lateral flow rate, and color. Lateral flow refers to liquid flow in which all of the sample and reagents components are carried at substantially equal rates and with relatively unimpaired flow laterally through the matrix, as opposed to the preferential retain of one or more components of the liquid, such as a chromatographic separation of the sample components.

The flow matrix material preferably possesses the following characteristics: (1) low non-specific affinity for sample materials and labeled specific binding reagents, (2) ability to transport a liquid by capillary action over a distance with a consistent liquid flow across the matrix, and (3) ready binding to immobilized specific binding reagents, (e.g., by covalent or non-covalent attachment or by physical entrapment). Materials possessing these characteristics include fibrous mats composed of synthetic or natural fibers (e.g., glass or cellulose-based materials or thermoplastic polymers, such as, polyethylene, polypropylene, or polyester); sintered structures composed of particulate materials (e.g., glass or various thermoplastic polymers); or cast membrane films composed of nitrocellulose, nylon, polysulfone or the like (generally synthetic in nature). The invention may utilize a flow matrix composed of sintered, fine particles of polyethylene, commonly known as porous polyethylene; preferably, such materials possess a density of between 0.35 and 0.55 grams per cubic centimeter, a pore size of between 5 and 40 microns, and a void volume of between 40 and 60 percent. Particulate polyethylene composed of cross-linked or ultra high molecular weight polyethylene is preferable. A flow matrix composed of porous polyethylene possesses all of the desirable features listed above, and in addition, is easily fabricated into various sizes and shapes.

The porous carrier matrix may be made from a material which has a low affinity for the analyte and test reagents. This is to minimize or avoid pretreatment of the test matrix to prevent nonspecific binding of analyte and/or reagents. However, materials that require pretreatment may provide advantages over materials that do no require pretreatment. Therefore, materials need not be avoided simply because they require pretreatment. Hydrophilic matrices generally decrease the amount of non-specific binding to the matrix.

In one aspect, the porous carrier matrix has an open pore structure with an average pore diameter of 1 to 250 micrometers and, in further aspects, about 3 to 100 micrometers, or about 10 to about 50 micrometers. The matrixes are from a few mils (0.001 in) to several mils in thickness, typically in the range of from 5 or 10 mils and up to 200 mils. The matrix should be translucent to allow for the visualization or photometric determination of the light and or color throughout the thickness of the matrix. The matrix may be backed with a generally water impervious layer, or may be totally free standing.

An example of a suitable porous carrier matrix in which lateral flow occurs is the high density or ultra high molecular weight polyethylene sheet material manufactured by Porex Technologies Corp. of Fairburn, Ga., USA. This material is made from fusing spherical particles of ultra-high molecular weight polyethylene (UHWM-PE) by sintering. This creates a porous structure with an average pore size of eight to 20 microns, depending on the size of the particles (20 to 60 microns, respectively). The polyethylene surface is treated with an oxygen plasma and then coated with alternating layers of polyethylenimine (PEI) and poly acylic acid (PAA) to create surfactant-free hydrophilic surface having wicking rate of 0.01-0.5 cm/s.

While matrices made of polyethylene have been found to be highly satisfactory, lateral flow materials formed of other olefin or other thermoplastic materials, e.g., polyvinyl chloride, polyvinyl acetate, copolymers of vinyl acetate and vinyl chloride, polyamide, polycarbonate, polystyrene, etc., can be used. Examples of suitable materials include Magna Nylon Supported Membrane from GE Osmonics (Minnetonka, Minn.), Novylon Nylon Membrane from CUNO Inc (Meriden, Conn.) and Durapore Membrane from Millipore (Billerica, Mass.).

The matrix materials may be slit, cut, die-cut or punched into a variety of shapes prior to incorporation into a device. Examples of alternative shapes of the matrix include circular, square/rectangular-shaped, flattened ellipse shaped or triangularly shaped. While not a focus of the invention, if desired, biological reagents may be applied to the materials before or after forming the desired shape. Biological reagents may be attached to the materials by any available method, for example, either by passively, diffusively, non-diffusively, by absorption, or covalently, depending upon the application and the assay.

A "conjugate reagent" is specific binding partner or binding partner of the analyte and is a molecule, such as a receptor, binding protein, antibody or antibody fragment, or enzyme (which binds to its substrate), that possesses the ability to interact with another molecule in a highly specific polar and spatial manner. The conjugate reagent also includes a label, or a moiety that is capable of binding to a label. For example, the conjugate reagent may include a specific binding partner for the analyte attached to a label. The attachment of the binding partner to the label may be accomplished covalently or non-covalently by any procedure well known to those of skill in the art. The label may be indirectly attached to the binding partner, such as through a biotin/avidin interaction, where the label is attached to biotin and the binding partner is attached to streptavidin.

By "immobilized binding reagent" is meant a molecule which is bound to a solid support and which has a specific affinity for an analyte of interest. Preferably, the affinity arises by virtue of the reagent possessing a complementary three-dimensional structure to the analyte, for example, as seen in a specific binding relationship such as the relationship between an enzyme and a substrate or an antigen and an antibody. Within a given pair, either member may be considered to be the analyte or the binding reagent. The definition serves only to differentiate the component to be detected in the sample (the analyte) from the reagent included in the device or method (an analyte binding partner).

Examples of analyte:binding reagent pairs include, without limitation, all of the following: a pathogen (for example, a bacteria, virus, fungus, filarial parasite, or protozoan); a soluble protein (for example, a growth factor, a lymphokine, a toxin, or a hormone); or a cell-surface protein or carbohydrate (for example, a cell adhesion molecule, a laminin, a fibronectin, an integrin, or a lectin) and a specific antibody or a specific receptor. Such pair may also include drugs, metabolites, pesticides, or pollutants and receptors specific to each.

A "label" is any molecule that is bound (via covalent or non-covalent means, alone or encapsulated) to another molecule or solid support and that is chosen for specific characteristics that allow detection of the labeled molecule. Generally, labels are comprised of, but are not limited to, the following types: particulate metal and metal-derivatives, dyed latex particles, radioisotopes, catalytic or enzyme-based reactants, chromogenic substrates and chromophores, fluorescent and chemiluminescent molecules, and phosphors. The utilization of a label produces a signal that may be detected by means such as detection of electromagnetic radiation or direct visualization, and that can optionally be measured. In one aspect, the label is associated with the conjugate reagent, wherein the label and the binding partner for the analyte are components of the conjugate reagent.

By "lance" is meant a component which is capable of piercing the seal of a liquid reagent container. Such a lance may also include a wick which facilitates flow of the liquid reagents out of their storage container and into the flow path matrix.

By "liquid reagents" is meant detector and/or wash solutions or reagents. A wash reagent is a liquid reagent that serves to remove unbound material from the detection zone having an immobilized binding reagent. A detector reagent is a liquid reagent that serves to both remove unbound material from the detection zone and to facilitate analyte detection.

In one such aspect the invention is directed to a device for the quantitative or qualitative detection of an analyte in a liquid sample. The device includes a flow path matrix that provides fluidic movement by capillary force. A sample application element receives the sample and transfers the sample to a first region of the matrix. The sample receiving element includes a non-porous carrier having a conjugate reagent that is solubilized by the sample liquid.

The sample application element generally includes an opening through which sample can be deposited on the matrix and a liquid containment reservoir. Such a containment reservoir can be utilized in any configuration or shape, and in one aspect is a well. The well can be cylindrical, conical, rectangular, square, oval or the like or a combination thereof. The dimensions of the well can also be varied widely according to the particular assay to be conducted and the shape of the well. Generally, the well should have a volume of 10-1000 μl and the walls should be sloped sufficiently to cause the liquid to flow freely to the opening at the bottom. The opening will generally be small, usually 0.3-15 mm$^2$, square, oval, triangular, round and the like.

The element is made of a non-absorbent and non-porous material. Generally, a non-porous rigid plastic polymer structure will suffice. A solubilizable conjugate reagent is present on a surface of the sample application element. In its simplest form, the conjugate reagent is present in a dried form on the surface of a well having a hole in contact with the matrix. In another aspect, the element includes a rigid structure that is molded into the element in order to increase the surface area that contacts the sample. For example, the structure may include a grating on the surface of the well, a mesh or screen structure within the well, or the well may include a series molded protrusions within the well. In another aspect, the carrier is a bead or a disk structure that has a non-porous surface. The carrier is retained in a chamber that receives liquid sample from the well. The element is configured to maximize the amount of fluid that contacts the surface of the bead. For example, the element retains the carrier in a chamber so that the sample can flow around the entire surface of the carrier with minimal clearance between the carrier and the walls of the chamber. In other embodiments, the structure includes a screen or other non-fibrous mesh that allows for the unimpeded flow of sample through the element.

The conjugate reagent is readily solubilized by a sample solution, which is present in the element for only a short amount of time, i.e., the time it takes for the sample to drain from the element into the matrix. In one aspect, the conjugate reagent is immediately solubilized upon the addition of the sample solution to the element.

In one embodiment of the invention, the sample application element includes a porous carrier that provides the surface for the dried conjugate reagents. Porous materials suitable for the carrier include natural, synthetic, or naturally occurring or synthetically modified materials: papers (fibrous) or membranes (microporous) of cellulose materials such as paper, cellulose, and cellulose derivatives such as cellulose acetate and nitrocellulose, fiberglass, glass fiber, cloth, both naturally occurring (e.g., cotton) and synthetic (e.g., nylon); porous gels such as silica gel, agarose, dextran, and gelatin; porous fibrous matrixes; starch based materials, cross-linked dextran chains; ceramic materials; olefin or thermoplastic materials including films of polyvinyl chloride, polyethylene, polyvinyl acetate, polyamide, polycarbonate, polystyrene, copolymers of vinyl acetate and vinyl chloride and combinations of polyvinyl chloride-silica; and the like. This list is representative, and not meant to be limiting. The porous carrier may be held in the sample application element by any common means, including those suitable for the non-porous carrier as described herein.

In another aspect, the sample application element includes a filter to remove particular matter before the sample liquid enters the matrix Many known materials are suitable for the filter, including the materials useful for the porous carrier. The filter should have a pore size of 1-100 microns, and have a thickness of 1-25 mils. The filter can act as the porous carrier, wherein the filter both removes unwanted particulate matter, and provides a surface for the dried conjugate reagent. The filter may be positioned underneath the sample application element, so that the sample liquid contacts the filter after the liquid has contacted the carrier and solubilized the conjugate reagent on the carrier. The filter may also be positioned such that the sample contacts the filter before contacting the carrier.

When the liquid sample is added to the sample application element, the conjugate reagent is solubilized and, depending upon the assay format, the conjugate reagent may specifically bind to an analyte in the sample to form a complex of the analyte and the conjugate reagent. In another aspect, the conjugate reagent includes an analyte analog, which does not complex with the analyte. The sample liquid containing the analyte and the conjugate reagent, whether complexed or not, flows into a first region of the matrix and are transported by capillary force in all directions within the matrix.

When the porous carrier matrix is in the form of a strip, the liquid from the first region will flow towards both ends of the strip. The liquid flows towards a second region of the strip containing a detection zone, which includes analyte binding partner that is immobilized at a discreet location on the matrix. Analyte and analyte analog in the liquid, if any, bind to the immobilized binding partner. The conjugate reagent, which includes a label or a moiety that can bind to a label, is immobilized in the region. The label can be detected by methods well known to those skilled in the art of lateral flow assays.

To facilitate detection, unbound material can be washed from the detection zone. In one aspect, a liquid reagent is stored on the device a sealed container. The device provides a liquid transfer element for accessing the liquid reagent in the sealed containers and transferring the reagent to the matrix. The device may include additional reagents, storage containers and conducting elements as well.

In a specific embodiment of the invention, the matrix is a flow path that has a first region in contact with sample application element, a second region that serves as the detection zone with one or more immobilized binding reagents, and a third region for entry of the liquid reagent. In operation, the sample migrates by capillary action from the first region of the matrix towards both the second and third regions. Liquid reagent then flows from the third region, past the first region and through the detection zone.

In one aspect, the first region that is in contact with the sample application element is positioned between the second region, which includes the detection zone, and the third region, which allows for entry of liquid reagents. Therefore, as the liquid reagent flows from the third region towards the detection zone, it forces all of the liquid sample through the detection zone. Because undiluted samples are used in the device, the ability of the device to allow the entire volume of the sample to flow through the detection zone maximizes the sensitivity of the assay. In addition, because the sample application zone lies between the third region and the detection zone, and because there is an unidirectional flow of sample once the wash reagent is added to the third region, all of the immobilized reagent in the detection zone are exposed to the same volume of sample, which ensures consistency of the assay.

In order to facilitate the capillary flow of the entire sample and the liquid reagent through the detection zone, the device includes an absorbent reservoir to absorb excess liquid. The excess fluid capacity of the reservoir ensures the flow of the entire liquid sample through the detection zone, and the ability of the liquid reagent to wash the detection zone of unbound analyte and conjugate reagent.

Materials suitable for use as an absorbent reservoir are preferably highly absorbent, provide capacity in excess of the volume of the fluid sample plus the added liquid reagents, and are capable of absorbing liquids from the flow matrix by physical contact as the sole means of fluid transfer between the two materials. A variety of materials and structures are consistent with these requirements. Fibrous structures of natural and synthetic fibers such as cellulose and derivatized cellulose (e.g., cellulose acetate) are preferred for this use. The fibers of the material may be oriented along a particular axis (i.e., aligned), or they may be random. A preferred embodiment of the invention utilizes non-aligned cellulose acetate fibers of density range 0.1 to 0.3 grams per cubic centimeter and void volume of 60 to 95 percent. A particularly preferred material is American Filtrona Corporation R-13948 Transorb Reservoir (Richmond, Va.).

In one aspect, the liquid reagent is contacted with the flow path when the operator activates the device by mechanically pressing the two halves of the devices together, which begins the flow of liquid reagents from storage containers into the flow path (for example, by piercing a storage container containing the reagents). The device includes an attachment structure that attaches the sample application element to the device. The structure maintains the sample application element in contact with the matrix but provides a mechanism that releases the contact between the element and the matrix upon operator activation of the device. Upon activation, a portion of the device that retains the matrix is moved in relation to the structure, thereby releasing the matrix from contact with the structure.

Disconnection of the sample application element from the matrix prevents flow of residual sample and conjugate reagent from the sample application element into the matrix. Because activation of the device provides for the flow of a detector reagent over the matrix, including flow past the area of the matrix in contact with the sample application element, any conjugate reagent that enters the matrix will react with the detector reagent as it flows towards the detection zone. If residual conjugate reagent continues to enter the matrix, the detection reaction may occur to some extent all along the matrix in the direction of the flow from the sample application element to the detection zone. Thus, the matrix may become streaked with label that is not bound in the detection zone.

The overall sequencing of the above steps is therefore controlled by the flow of the liquid within the flow path matrix and the physical positioning of the sample application element and liquid reagent entry and exit regions relative to the position of the deposited immobilized binding reagent. Operator involvement is, in general, limited to a maximum of three steps: application of the sample, one-step release of stored liquid reagents (that is, detector and/or wash solutions), and mechanical contacting of the absorbent reservoir with the flow path matrix. Moreover, the one-step release of stored liquid reagents and mechanical contacting of the absorbent reservoir with the flow path matrix can be coupled into one step. Also optionally occurring during this step, the contact between the matrix and sample application element is released.

The sample application element can be secured to the device to provide releasable contact with the flow path matrix by any known means that provides fluidic communication between the matrix and the element. In one aspect of the invention, operator activation breaks the fluidic communication. For example, the sample application element may be secured to an outer housing of the device so that the flow path matrix and the element can be held together to prevent the flow path matrix and the element from separating before activation. After operator activation that moves an inner housing holding the matrix in relation to the outer housing, the fluidic communication between the sample application element and the flow path is broken because the element remains secured to the outer housing.

In one embodiment, the device includes a wash and/or detector reagent in sealed container(s) and a means, for example a lance with a wick, for introducing the reagent(s) into the third region of the flow path, for example, by piercing the sealed containers. Such a lance may also include a wick that facilitates flow of the liquid reagents out of their storage containers and into the flow path.

Referring now to FIGS. 1-4, an example of a device 10 is shown in both the un-activated (FIGS. 1 and 3) and the activated (FIG. 4) configuration. The device 10 includes a two-part housing having an upper housing portion 12 that retains a flow path matrix 14 and secures a sample application element 16. A lower housing portion 18 includes reagent containers 20 and 22, and an absorbent pad 24. The upper housing portion 12 provides a window 28 that allows an operator to visually monitor assay results at a detection zone 30 of the matrix 14. Immobilized binding reagent 32 is shown in the detection zone 30 as dots. However, any shape can be used, including + or − signs, dashes, or any other shape that can provide a visual signal to the operator. The relative sizes of components of the device 10 can vary and the proportions depicted in the figures herein are for illustrative purposes only.

Figure 1:
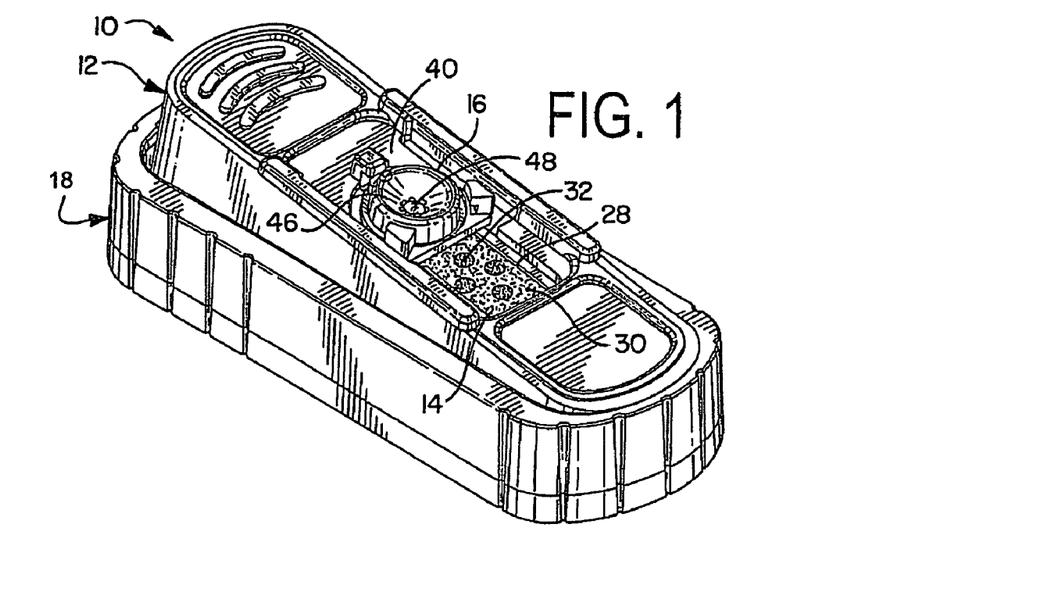
FIG. 1 is a side plan view of an embodiment of the device of the invention. The device is shown prior to activation by the operator.
Figure 3:
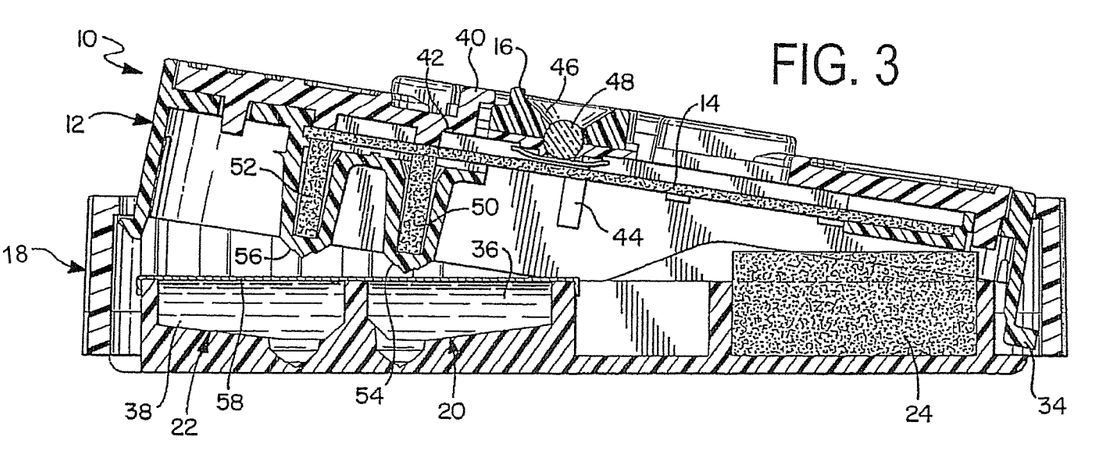
FIG. 3 is a cross sectional illustration of the device of FIG. 1.
Figure 4:
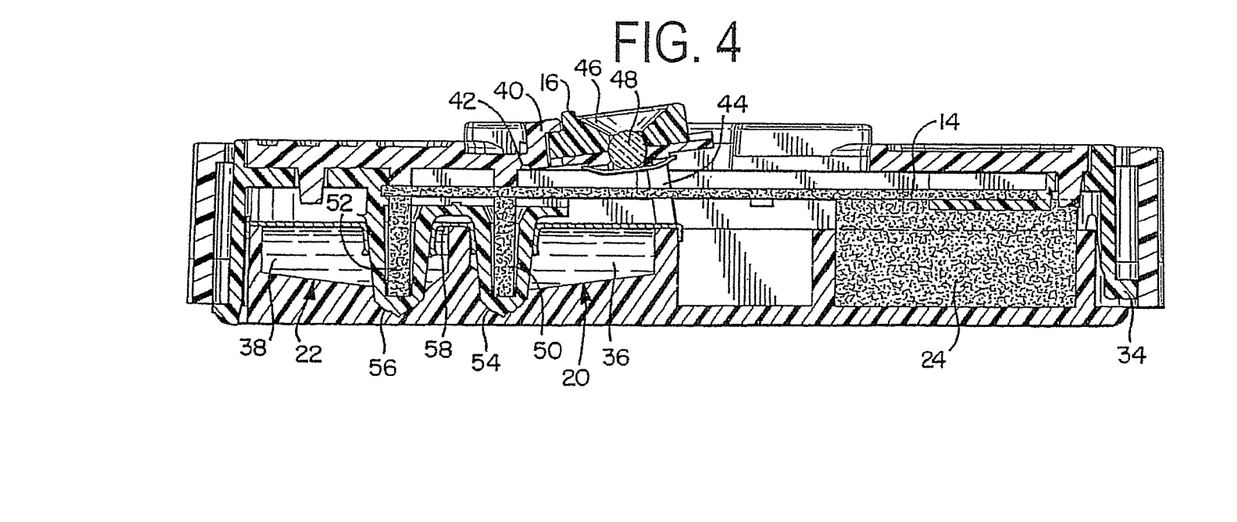
FIG. 4 is a cross sectional illustration of the device of FIG. 1. The device is shown after activation by the operator.

The upper housing portion 12 and the lower housing portion 18 are pivotably disposed with respect to each other by means of a hinge 34. The pivotal connection initially holds the two portions of the housing in a pre-activated configuration prior to the addition of a sample liquid to the sample application element 16. Operator activation is accomplished by squeezing the upper and lower housing portions 12 and 18 together, which causes the flow path 14 to contact the absorbent pad 24. Activation also releases the liquid reagents 36 and 38 from the sealed containers 20 and 22 enabling flow of the liquid reagents into the flow path matrix 14.

Figure 2:
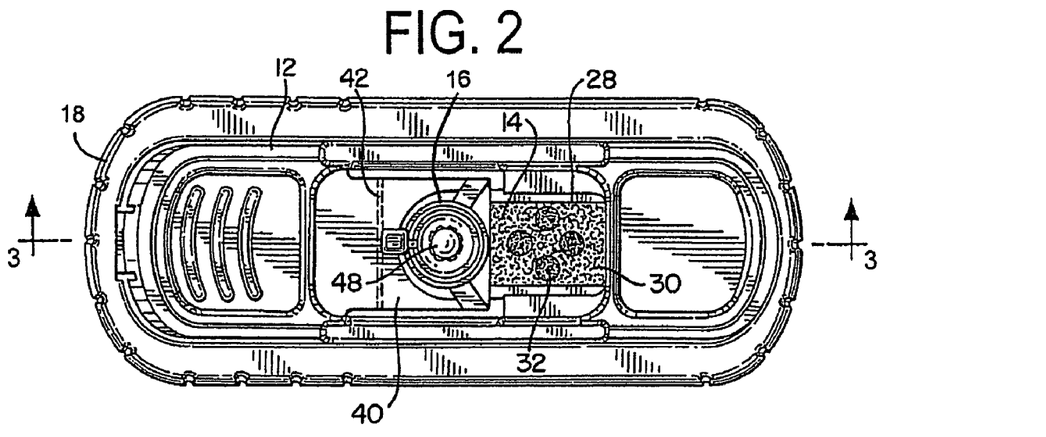
FIG. 2 is a top plan view of an embodiment of the device of the invention.

The sample application element 16 is attached to the upper housing 18 by an attachment structure 40 that supports the sample application element 16 and provides for releasable contact between the sample application element 16 and the matrix 14. Prior to activation of the device, the sample application element 16 is in physical contact with the matrix 14. The attachment structure 40 can be any physical structure that, upon activation of the device, causes the sample application element 16 to no longer contact the matrix 14. As shown in FIGS. 2, 3 and 4, the attachment structure 40 can include a hinge 42 that is molded as a line of weakness into the upper housing portion 12.

As shown in FIGS. 3 and 4, the release in contact between the sample application element 16 and the matrix 14 is directed by a post 44 which protrudes from the underside of the attachment structure 40. Upon activation, the post 44 contacts a portion of the lower housing, which stops the movement of the structure 40 in relation to the lower housing 18. When the movement of the structure 40 has been stopped in relation to the lower housing portion 18, the upper housing portion 12 continues to move towards the lower housing portion 18. The attachment structure 40 pivots along hinge 42, which results in a release in the contact between the element 16 and the matrix 14. Other ways of releasing contact between the sample application element and the matrix could readily be accomplished, and the post 44 and hinge 42 are only one example.

To carry out a binding assay using the device 10, fluid sample containing an analyte is applied through the sample application element 16. As shown in FIGS. 3 and 4, the sample application element includes a well 46 and bead 48, which is non-absorbent and is coated with a dried conjugate reagent. When the liquid the sample is applied to the well 46, the sample flows over the bead 48 and dissolves the conjugate reagent. In a sandwich assay format, for example, any analyte in the sample binds with the conjugate reagent and the sample fluid flows into a first region of the flow path matrix 14 that is in the general area of contact with the element 16.

Referring again to FIGS. 3 and 4, once the sample is added to matrix 14 through the element 16, the sample liquid will flow towards a second region of the matrix 14 that contains the detection zone 30 and towards a third region of the matrix that is near the reagent containers 20 and 22. The operator then activates the device by pressing together the upper housing 12 and the lower housing 18. Activation of the device causes the liquid reagents 36 and 38 to be released from containers 20 and 22 into the third region of the matrix 14. The reagents flow towards the second region, which forces all of the sample liquid towards and through the detection zone 30. Once the matrix 14 is saturated, capillary flow is maintained by the liquid absorption into reservoir pad 24. The reservoir pad 24 is positioned toward one end of the flow path 14 and after the detection zone 30 so as to draw the fluid through the detection zone and out of the flow path matrix 14.

In the device illustrated in FIGS. 3 and 4, the liquid reagents may include a wash reagent 36 and a detector reagent 38. The wash reagent 36 is stored reagent container 20 and is delivered, by the wash reagent delivery wick 50 into the third region of the flow path 14. The purpose of the wash reagent 36 is to transport unbound sample and unbound conjugate reagent along the flow path 14 and away from the detection zone 30 into the absorbent pad 24.

The detector reagent 38 stored in the reagent container 22 and is delivered, by the detector reagent delivery wick 52 into the third region of the flow path 14. The detector reagent 30 facilitates analyte detection. The device depicted in FIGS. 3 and 4 illustrates a physical linkage of the delivery wicks 50 and 52 within the lances 54 and 56 that serve to both pierce the seal 58 of the reagent containers 20 and 22 and deliver the reagent to the flow path. This linkage facilitates the release of the two stored liquid reagents with a single action. Sequential utilization of the two reagents, i.e., wash reagent followed by detector reagent, is accomplished by delivering the wash reagent closer to the absorbent reservoir 24 than the detector reagent. Fluid flow toward the absorbent reservoir 24 after activation causes the wash reagent 36 be pulled into the flow path 14 by capillary force. Once a volume of the wash reagent 36 been absorbed into the flow path matrix 14, displacing unbound sample and unbound conjugate reagent, the detector reagent 38 is delivered into the flow path matrix 14 by capillary force. Detector reagent 38 displaces the wash reagent 36 in the direction of the absorbent reservoir 24. When the detector reagent 38 flows into the detection zone 30, complex formation is detectable, and the assay procedure is complete. The detector reagent 38 may comprise a substrate that provides a detectable signal in the presence of the sample analyte-conjugate complex. The detector reagent may contain a substrate, reactant, or any suitable reagent that, when brought in contact with the captured labeled specific binding reagent, produces a detectable reaction.

Figure 5:
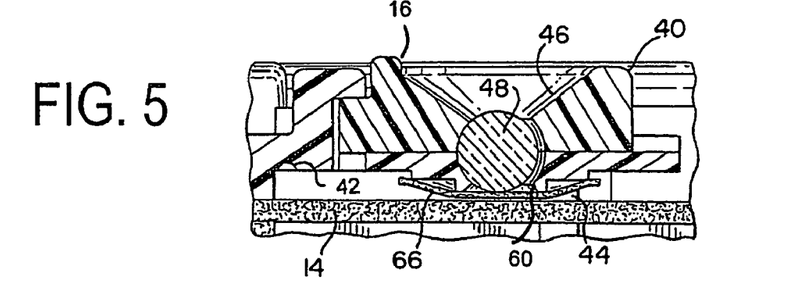
FIG. 5 is a detail view of the portion of the device shown positioned prior to activation of the device.
Figure 6:
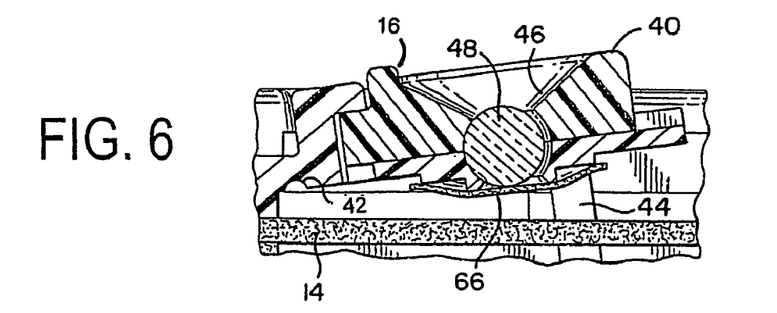
FIG. 6 is a detail view of the portion of the device shown in FIG. 5 after operator activation.
Figure 7:
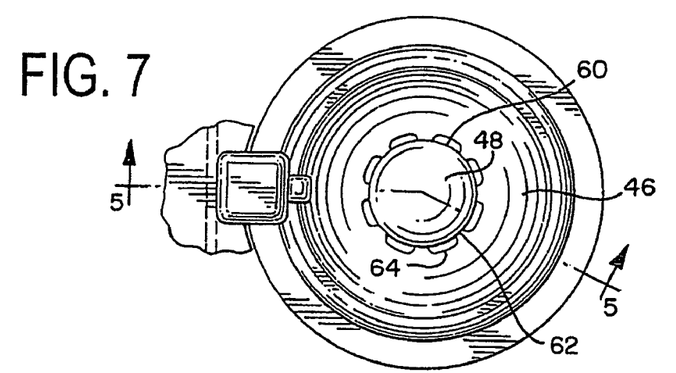
FIG. 7 is a top plan view of one embodiment of the sample application element.
Figure 8:
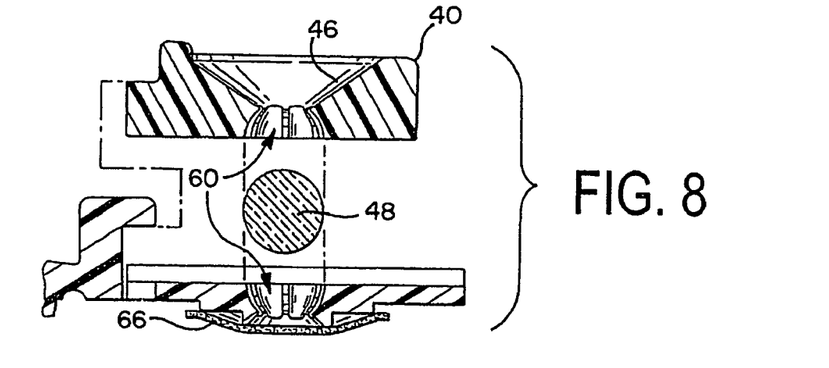
FIG. 8 is an exploded view of the embodiment of the sample application element shown in FIG. 7.

Various configurations for the sample application element can be used. As one example, FIGS. 5, 6, 7 and -8 show the sample application element 16 in the form of a well 46 leading to a chamber 60 that retains the bead 44. In this particular embodiment, the chamber 60 has ribs 62 that confine the bead while the space 64 between the ribs 62 allows for the sample to flow freely around the bead. The sample application element may include filter 66 that removes interfering particulate matter from the sample before the sample enters the flow path matrix. The filter is optional depending upon the analyte to be detected and the type of sample.

Figure 9:
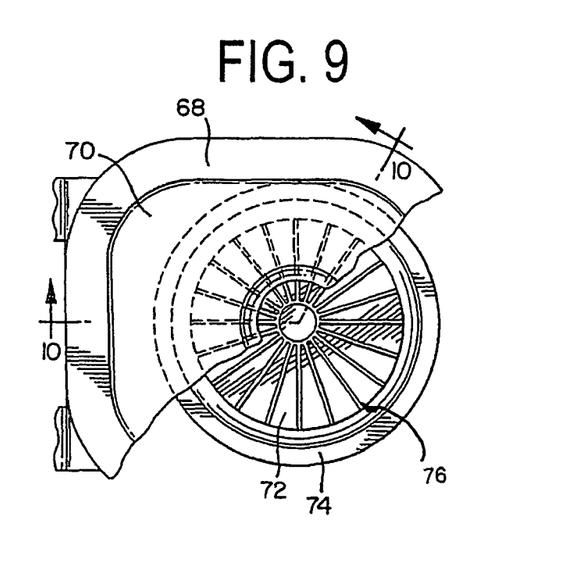
FIG. 9 is a top plan view of an embodiment of the sample application element.
Figure 10:
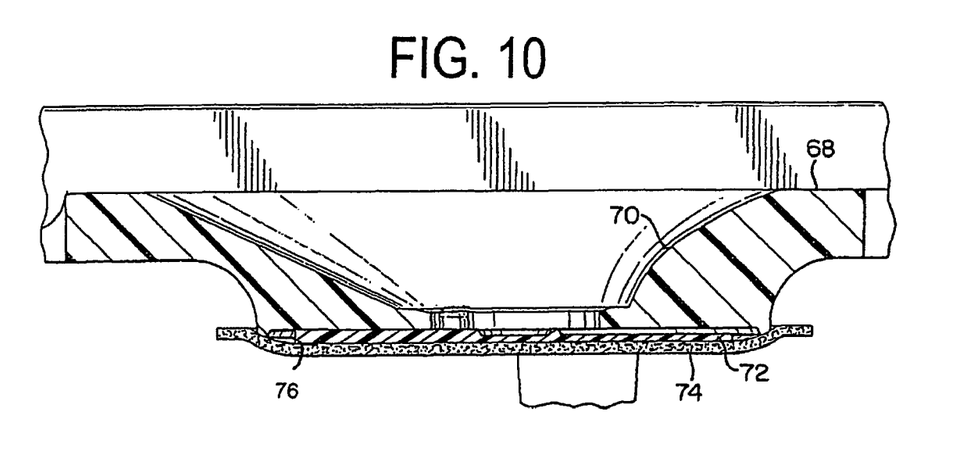
FIG. 10 is a cross-sectional view of the sample application element shown in FIG. 9.

Referring now to FIGS. 9 and 10, another embodiment of the sample application element 68 is shown. Here the sample application element includes well 70 and disk 72, which is non-absorbent and coated with a dried conjugate reagent. Also shown is optional filter 74. Sample liquid that is added to the well 70 flows over and around disk 72 and solubilizes the dried reagent before entering the flow path matrix 14. In this embodiment, the disk includes ridges 76 to increase the surface area of the disk, to slow the sample flow and to increase sample and reagent mixing. Alternately, well 70 can have a convex central portion and peripheral slots to direct the sample to the outer periphery of disc 72. In this embodiment, the sample will flow inward on disc 72 to a central aperture before reaching matrix 14.

In another aspect, the filter or other porous carrier includes the dried conjugate reagent. When the porous carrier is independent of the filter, the carrier can be associated with the sample application element by any readily known means.

Other configurations of a sample application element can be readily devised. The element should include a carrier with surface area to retain a sufficient amount of dried reagent, which can be readily solubilized by the sample liquid. The sample application element should be include a structure for attaching the element to the housing that allows for releasable contact between the element and the flow path matrix.

The device of the invention facilitates assays that are of low background and high specificity. In addition, the semi-automated nature of the assay devices and methods of the invention significantly reduces the level of technical sophistication required of an individual performing the binding assays described herein, facilitating assays that may be carried out in an environment remote from a laboratory and by practitioners with limited training.

Any or all of the above embodiments of the invention may be provided as a kit. In one particular example, such a kit would include a device of the invention complete with specific binding reagents, for example, the dried conjugate reagent and immobilized binding reagents, as well as wash reagent and detector reagent. Positive and negative control reagents may also be included, if desired or appropriate. In addition, other additives may be included, such as stabilizers, buffers, and the like. The relative amounts of the various reagents may be varied widely, to provide for concentrations in solution of the reagents that substantially optimize the sensitivity of the assay.

In an alternative device according to the invention, the detector reagent acts both to remove unbound sample and reagents from the detection zone and to facilitate analyte detection. Such a device may be designed essentially as shown in FIGS. 3 and 4, except that the device includes a single reagent storage vessel and a single reagent delivery wick (for example, included as a component of the lance). As described above, sample is added to the device via the sample application element and, at some point after addition, the device is operator activated (as described above). The detector reagent storage vessel is pierced by the lance (containing a delivery wick) and the detector reagent delivered to the flow path matrix. Activation draws the detector reagent into the flow path matrix by capillary force. As the detector reagent flows towards the absorbent reservoir, it displaces the fluid in the flow path matrix, clearing the matrix, and importantly, clearing the detection zone of unbound material.

The conjugate reagent may be labeled with a radioactive, fluorescent, or light-absorbing molecule. In such a case, the detector reagent acts merely as a wash solution facilitating detection of complex formation at the detection zone by washing away unbound labeled reagent.

The conjugate reagent may also be labeled with an enzyme. In such a case, the detector reagent includes a substrate that produces a detectable signal upon reaction with the enzyme-labeled conjugate-analyte complex at the detection zone. In another aspect, the conjugate reagent has a visible label, such as a colloidal gold. The liquid wash reagent removes any unbound visible label from the detection zone.

In another embodiment, a analyte analog may be used, for example, to compete with the analogous target analyte for binding to the specific binding partner (that is, competition assay). An analyte analog is a specific derivative of the target analyte that may be optionally attached, either covalently or non-covalently, to other chemical species (for example, a label).

To ensure proper operation, any of the devices described herein may further include various other binding reagents immobilized at the detection zone 30 at positions distinct from the immobilized binding reagent that is specific for the analyte. For example, an immunoreagent that recognizes the species-specific portion of a labeled conjugate binding reagent or the enzyme portion of an enzyme-labeled reagent may be included as a positive control to assess the viability of the reagents within the device. Additionally, a reagent, for example an antibody isolated from a non-immune member of the species from which the antibody portion of the immobilized binding reagent was derived, may be included as a negative control to assess the specificity of immunocomplex formation.

The invention may be used to detect multiple analytes in a single sample. For example, two or more distinct analyte specific binding partners may be immobilized in the detection zone. The sample application element may include two or more different conjugate reagents that have binding partners that are specific for the different analytes. When more than on analyte is detected, the labels associated with each analyte must be distinguishable, such as by the locations of the binding partners in the detection zone.

The basic components of the invention may be packaged as a single unit or housed as several units for multiple-sample devices. Various packaging options in which liquid reagent storage reservoirs or sample application element are shared between several flow matrix components may also be envisioned. In one particular example, the device contains multiple regions within the detection zone, each including a different immobilized binding reagent (for example, one may include an immobilized antibody specific for feline immunodeficiency virus and another may include an immobilized antibody specific for feline leukemia virus) and a single biological sample (for example, a sample of feline serum). The single sample is assayed for the presence of one or both viruses.

Preferably, the detection zone 30 is seen from the outside of the housing, allowing ready detection of assay results. The sample application element 16 is preferably designed such that the volume of the well is at least as large as the total volume of sample required to perform the assay. In addition, the absorbent reservoir 24 is preferably of sufficient size to accommodate the total volume of sample as well as all added liquid reagents, that is, detector reagent and wash reagent.

Although various specific embodiments of the present invention have been described herein, it is to be understood that the invention is not limited to those precise embodiments and that various changes or modifications can be affected therein by one skilled in the art without departing from the scope and spirit of the invention.

What is claimed is:

1. A device for determining the presence or amount of an analyte in a liquid sample, the device comprising a flow path matrix that provides fluidic movement by capillary force and a non-porous sample application element for receiving the sample and transferring the sample to a first region of the matrix, the matrix further comprising a second region comprising a detection zone laterally spaced from the first region, wherein the element comprises a non-porous carrier coated with a solubilizable conjugate reagent and wherein the element and the matrix are in contact upon application of the sample to the element, and the element and the matrix are associated with a housing configured to actuate disengagement of the contact between the element and the matrix upon activation of the device by an operator.

2. The device of claim 1 wherein the matrix comprises an immobilized analyte binding partner in the second region.

3. The device of claim 2 wherein the immobilized analyte binding partner is selected from the group consisting of an antigen, an antibody, a ligand, a receptor, and a nucleic acid molecule.

4. The device of claim 1, further comprising a filter for removing particular matter before the sample enters the matrix.

5. The device of claim 1 wherein the sample application element comprises a well and the carrier includes the inner surface of the well or a surface molded in the well.

6. The device of claim 1 wherein the sample application element comprises a well and a chamber that receives sample liquid from the well and that retains the carrier.

7. The device of claim 6 wherein the carrier comprises a bead.

8. The device of claim 1 wherein the carrier comprises a polymeric mesh, screen or grating structure.

9. The device of claim 1 wherein the housing configuration further comprises an attachment structure that provides the disengagement actuation between the element and the matrix.

10. The device of claim 1 further comprising at least one liquid reagent stored in at least one sealed container.

11. The device of claim 10 further comprising at least one liquid transfer element for releasing and transporting the at least one liquid reagent from the at least one sealed container to the matrix.

12. The device of claim 10 wherein the at least one liquid reagent is released from the at least one container upon activation of the device by the operator.

13. The device of claim 1 further comprising an absorbent reservoir for absorbing excess liquid from the matrix.

14. The device of claim 1 wherein the conjugate reagent comprises an analyte analog or comprises a binding partner for the analyte selected from the group consisting of an antigen, an antibody, a ligand, a receptor, and a nucleic acid molecule.

15. The device of claim 1 wherein the housing further comprises an upper housing portion and a lower housing portion pivotally disposed with respect to each other by a hinge.

16. A device for determining the presence or amount of an analyte in a liquid sample, the device comprising:
- a flow path matrix that provides fluid movement by capillary force, the flow path matrix further comprises:
  - (i) a third region for receiving one or more liquid reagents;
  - (ii) a second region comprising an immobilized analyte binding reagent; and
  - (iii) a first region for receiving an analyte-containing fluid sample, the first region being laterally positioned between the third region and a second region; and
- a non-porous sample application element for receiving the sample and transferring the sample to the first region, the element comprising a non-porous carrier coated with a conjugate reagent that is solubilized by the fluid sample, and wherein the element and the matrix are in contact upon application of the sample to the element and are associated with a housing configured to actuate disengagement of the contact between the element and the matrix upon activation of the device by an operator.

17. The device of claim 16 further comprising an attachment structure that provides the disengagement of the contact between the element and the matrix.

18. The device of claim 16, further comprising a filter for removing particular matter before the sample enters the matrix.

19. The device of claim 16 wherein the sample application element comprises a well and the carrier includes an inner surface of the well or a surface molded in the well.

20. The device of claim 16 wherein the sample application element comprises a well and a chamber that receives the sample from the well and retains the carrier.

21. The device of claim 20 wherein the carrier comprises a bead.

22. The device of claim 16 wherein the carrier comprises a polymeric mesh, screen or grating structure.

23. The device of claim 16 further comprising at least one liquid reagent stored in at least one sealed container.

24. The device of claim 23 wherein the at least one liquid reagent comprises at least one of a wash reagent and a detector reagent.

25. The device of claim 24 further comprising at least one liquid transfer element for releasing and transporting the at least one liquid reagent from the at least one sealed container to the third region.

26. The device of claim 25 wherein the at least one liquid transfer element comprises a wick.

27. The device of claim 23 wherein the at least one liquid reagent is released from the at least one container upon activation of the device by the operator.

28. The device of claim 16 further comprising an absorbent reservoir for absorbing excess liquid from the flow path matrix.

29. The device of claim 16 wherein the conjugate reagent comprises an analyte analog, or a binding partner for the analyte selected from the group consisting of an antigen, antibody, ligand, receptor, and nucleic acid molecules.

30. The device of claim 16 wherein the immobilized analyte binding reagent is selected from the group consisting of an antigen, antibody, ligand, receptor, nucleic acid molecule, chemically reactive groups and fragments thereof.

31. The device of claim 16 wherein the housing further comprises an upper housing portion and a lower housing portion pivotally disposed with respect to each other by a hinge.

32. A device for determining the presence or amount of an analyte in a liquid sample, the device comprising (a) a flow path matrix that provides lateral flow of the liquid sample, (b) a non-porous sample application element comprising a non-absorbent and non-fibrous structure coated with a dried conjugate reagent that is solubilized by the sample upon addition of the sample to the element, and (c) a means for actuating disengagement between the element and the matrix upon activation of the device, wherein the element delivers the sample to a first region of the matrix that is in fluid communication with the element upon application of the sample to the element, and wherein the matrix further comprises a second region comprising an immobilized binding partner for the analyte, wherein the second region is laterally spaced from the first region.

* * * * *